US011744780B2

(12) United States Patent
Gharibian et al.

(10) Patent No.: US 11,744,780 B2
(45) Date of Patent: Sep. 5, 2023

(54) TEETHING SYSTEM

(71) Applicant: FRIDABABY, LLC, Miami, FL (US)

(72) Inventors: Nairi Gharibian, Glendale, CA (US); Chelsea Hirschhorn, Miami, FL (US); Sam Sauceda, El Serino, CA (US); Gregary Hack, Aventura, FL (US); Maria Level, Miami, FL (US)

(73) Assignee: FRIDABABY, LLC, Miami, FL (US)

(*) Notice: Subject to any disclaimer, the term of this patent is extended or adjusted under 35 U.S.C. 154(b) by 176 days.

(21) Appl. No.: 17/474,310

(22) Filed: Sep. 14, 2021

(65) Prior Publication Data

US 2023/0080026 A1 Mar. 16, 2023

(51) Int. Cl.

*A61B 17/02* (2006.01)
*A61J 17/02* (2006.01)
*A61J 17/00* (2006.01)

(52) U.S. Cl.

CPC ............ *A61J 17/02* (2013.01); *A61J 17/107* (2020.05); *A61J 17/111* (2020.05); *A61J 2200/44* (2013.01)

(58) Field of Classification Search

CPC ............ A61H 13/00; A61H 2201/0153; A61H 2201/0221; A61J 17/02; A61J 2200/44; A61J 17/001; A61J 17/111; A61J 9/0623; A61J 17/10; A61J 11/00; A61J 11/0035; A61J 11/0075; A61J 17/00; A61J 17/107; A61J 17/109; A61J 17/1111; A61J 17/1115; A61J 17/113; A61J 2200/40; A61J 2200/50; A61J 9/0669

See application file for complete search history.

(56) References Cited

U.S. PATENT DOCUMENTS

| | | | | |
|---|---|---|---|---|
| 1,095,264 | A | 5/1914 | Bridges | |
| 2,115,405 | A | 4/1938 | Allen | |
| 2,514,844 | A | 7/1950 | Cohen | |
| 2,566,595 | A | 9/1951 | Cameron | |
| 5,013,321 | A | 5/1991 | MacVane | |
| 5,160,344 | A | 11/1992 | Werton | |
| 5,211,656 | A * | 5/1993 | Maddocks | A61J 17/113 606/236 |
| 5,658,314 | A | 8/1997 | Scheffer et al. | |
| D424,204 | S | 5/2000 | Jewell et al. | |
| 6,056,774 | A | 5/2000 | Johansen et al. | |
| D640,382 | S | 6/2011 | Roehrig et al. | |
| D657,471 | S | 4/2012 | Chin et al. | |
| D687,954 | S | 8/2013 | Dallman | |
| 8,518,079 | B2 | 8/2013 | Sarver | |
| D697,274 | S | 1/2014 | Thorne | |
| 9,295,616 | B2 | 3/2016 | Kellogg | |
| 9,744,104 | B1 | 8/2017 | Weston et al. | |
| 10,265,241 | B1 | 4/2019 | Paul | |
| 10,639,241 | B1 | 5/2020 | Torres et al. | |

(Continued)

*Primary Examiner* — Katherine M Shi

(74) *Attorney, Agent, or Firm* — PERKINS IP LAW GROUP LLC; Jefferson Perkins

(57) ABSTRACT

One or more biting elements of a teething system are cooled to below ambient temperature, while a handle of the teething system is left at ambient temperature. One of the biting elements is selected by the caregiver and is inserted into a receptacle in the handle. As assembled, a cooled teething surface on the biting element is exposed so that a baby may bite it, but at the same time the baby's hands are insulated by the handle from contacting the cooled biting element.

18 Claims, 7 Drawing Sheets

(56) References Cited

U.S. PATENT DOCUMENTS

| | | | | |
|---|---|---|---|---|
| 2005/0004603 | A1* | 1/2005 | Desousa | A61J 17/02 606/235 |
| 2014/0243895 | A1 | 8/2014 | Kellogg | |
| 2015/0374588 | A1 | 12/2015 | Strazzeri | |
| 2016/0184186 | A1 | 6/2016 | Montini et al. | |
| 2017/0215615 | A1 | 8/2017 | Prosise et al. | |
| 2018/0242764 | A1 | 8/2018 | Wynne | |
| 2019/0216682 | A1 | 7/2019 | Vreeland | |
| 2019/0290549 | A1 | 9/2019 | Qi et al. | |

* cited by examiner

TEETHING SYSTEM

BACKGROUND OF THE INVENTION

The eruption of first or "baby" teeth in an infant causes sore gums. Teethers have been developed that provide surfaces on which a baby or small child can bite or chew to ameliorate pain. Some teethers are provided with multiple teething surface shapes or textures to provide the caregiver or child with alternative choices.

It is also known to freeze or refrigerate teethers, such that the teething surface is cold, offering additional relief to the child. Unfortunately, when an entire teether is cooled to a temperature significantly below ambient, the teether tends to be too cold for the child to comfortably hold with his or her hands. U.S. Pat. No. 5,160,344 to Werton discloses a teething device in which one-half of a teething ring is left at ambient temperature, while the other half of the teething ring is cooled. The cooled half is then assembled to the warm half by means of tenons and sockets on the ends of the ring halves. Werton also discloses the joining together of entire rings, only one of which is cooled. In Werton, the child holds the warm (ambient) component while biting on the cooled component. However, no teething device has yet been developed that shrouds a major portion of the biting element from contact with the hand(s) of a child, or which is capable of insulating a nonselected teething surface while exposing a selected teething surface, or which can be used to insulate any of multiple cooled biting elements.

SUMMARY OF THE INVENTION

According to one aspect of the invention, a teething system includes a handle that is adapted to be grasped by one or both hands of a baby or small child. The handle has a receptacle with an open end. The handle is meant to stay at room or ambient temperature. The teething system further includes at least a first biting element with a first portion and a second portion. The first portion has a first teething surface formed thereon which the child may bite. The second portion, which is a major portion of the biting element, is adapted to be slid into the receptacle. The biting element is adapted to be cooled to a cooled temperature that is below the ambient temperature. Subsequent to cooling, the second portion of the biting element is slid into the handle, thereby assembling it to the handle. The first portion is exposed and the teething surface thereof is available for the child to bite. In this fashion, the baby's gums may be cooled by the teething surface, while at the same time the baby's hands are insulated from the cooled biting element.

In a related aspect of the invention, a teething system is provided that includes a handle with a receptacle. The system further includes a biting element that has a first portion and a second portion, each with respective teething surfaces. The handle is adapted to be left at ambient temperature while the biting element is adapted to be cooled to a cooled temperature that is below ambient temperature. The caregiver selects one of the two portions of the biting element for use. A nonselected portion is inserted into the handle receptacle, while the selected portion is left exposed, such that its teething surface is available for the child to bite it. The handle shrouds the nonselected portion of the biting element from contacting the hands of the child.

In yet another aspect of the invention, a teething system is provided which includes a handle with a receptacle. This handle is adapted to remain at ambient temperature. The teething system further includes plural biting elements, including first and second biting elements. These biting elements are each adapted to be cooled to a cooled temperature below ambient temperature. The first biting element has a first portion with a first teething surface formed thereon, and a second portion adapted to be inserted into the handle receptacle. The second biting element has a third portion with a second teething surface formed thereon, and a fourth portion adapted to be inserted into the handle receptacle. In use, one of the second and fourth portions is inserted into the handle receptacle, presenting one of the first and third portions to the small child to bite. The handle shrouds one of the second and fourth portions from contacting the hands of the child, while presenting a cooled teething surface to the child to bite.

In any of the above embodiments, the handle receptacle and the biting element may each be formed around an axis so as to be substantially bilaterally symmetrical. The biting element has a body with a straight first sidewall parallel to the axis, while the receptacle also has a straight first sidewall parallel to the axis. At least one first nub or bump is formed on the first sidewall of the biting element to laterally extend therefrom, so as to create an interference fit with the first sidewall of the handle receptacle. In one embodiment, the biting element has a straight second sidewall opposed to its first sidewall and disposed to be parallel to the axis. The handle receptacle likewise has a straight second sidewall opposed to its first sidewall and disposed to be parallel to the axis. At least one second nub or bump laterally extends from the second sidewall of the biting element body to engage the second sidewall of the receptacle, creating an interference fit between the biting element and the second sidewall of the receptacle of the handle. Because of these interferences, the biting element will not be removable from the handle receptacle without some force, and the biting element will stay assembled to the receptacle while the child is using the assembly.

In those embodiments that include more than one teething surface, the shape or texture of the teething surfaces may be chosen to be different from each other, so as to give the caregiver and the child alternatives for teething relief.

In one embodiment, the biting element(s) are hollow. In one embodiment, the biting element(s) are filled with a substance that is liquid at ambient temperature. In one embodiment, this substance freezes when cooled to the cooled temperature. The heat of fusion of the frozen substance may therefore provide enhanced cooling to the biting element for a longer period of time. In another embodiment, the substance stays in a liquid phase at the cooled temperature.

In a further aspect of the invention, a method is disclosed for providing relief to a child from teething pain. A handle with an open-ended receptacle is left at ambient temperature. A first biting element is cooled to a cooled temperature below ambient temperature. A second, major portion of the first biting element is inserted into the receptacle, so as to assemble the biting element to the handle. The assembled handle and biting element are offered to the child. Since the handle insulates the second portion of the biting element, the child may hold the handle of the assembly in comfort, while biting on the exposed, cooled teething surface. In one embodiment of the method, the caregiver selects which of first and second portions of the biting element will be used by the child, and inserts the nonselected portion into the handle receptacle. In one embodiment, the caregiver may select among a plurality of such biting elements for use.

BRIEF DESCRIPTION OF THE DRAWINGS

These and further aspects of the invention and their advantages can be discerned in the following detailed description as read in conjunction with the drawings of an exemplary embodiment, in which like characters denote like parts and in which.

DETAILED DESCRIPTION

Figure 1:
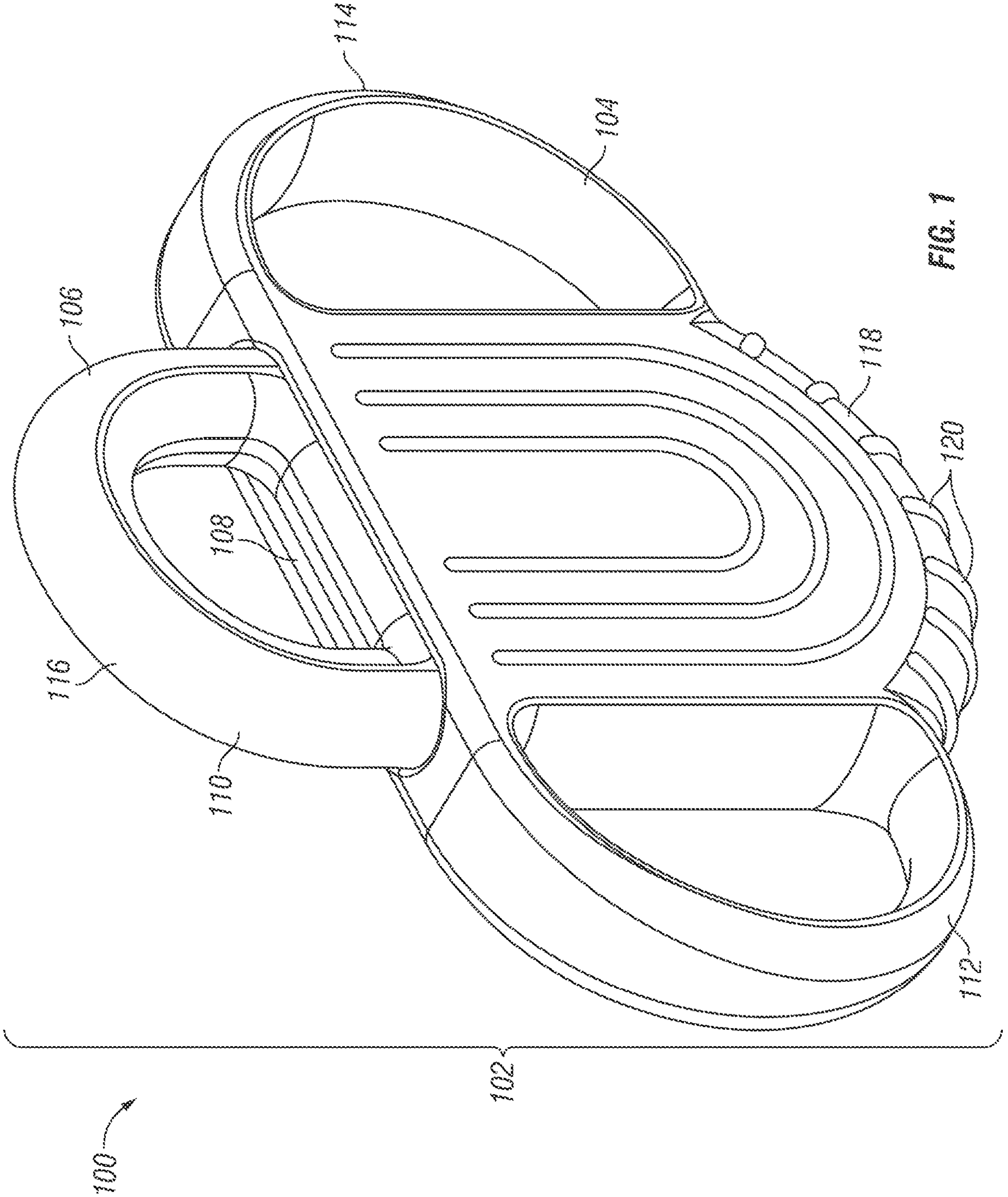
FIG. 1 is perspective view of an assembled teething system according to the invention, showing the assembly of a first biting element to a handle.

One embodiment of a teething system according to the invention is indicated generally at 100 in FIG. 1. In use, the system 100 comprises an assembly 102 that includes a handle 104 and at least one biting element 106 that is slid into a receptacle 108 in the handle 104. As so inserted, a first portion 110 of the biting element 106 is left exposed for the child to bite. A second, major portion of the biting element (not visible in this figure; see, e.g., FIG. 4) is insulated from the hands of the child by the handle 104.

In the illustrated embodiment, the handle 104 is integrally molded from a nontoxic polymer, and preferably a nontoxic elastomer. In one embodiment, the elastomer is silicone rubber.

A left handle wing 112 extends leftward from the handle receptacle 108, and a right handle wing 114 extends rightward from the handle receptacle 108. Wings 112, 114 are adapted to be grasped by the child while the child is biting the exposed teething surface 116 of first portion 110. In one embodiment, the handle 104 further includes an auxiliary teething surface 118 with a preselected shape and texture, in this case a convexly curved shape with a plurality of elongate ribs 120 formed thereon. Other shapes and textures could be chosen instead.

Figure 2:
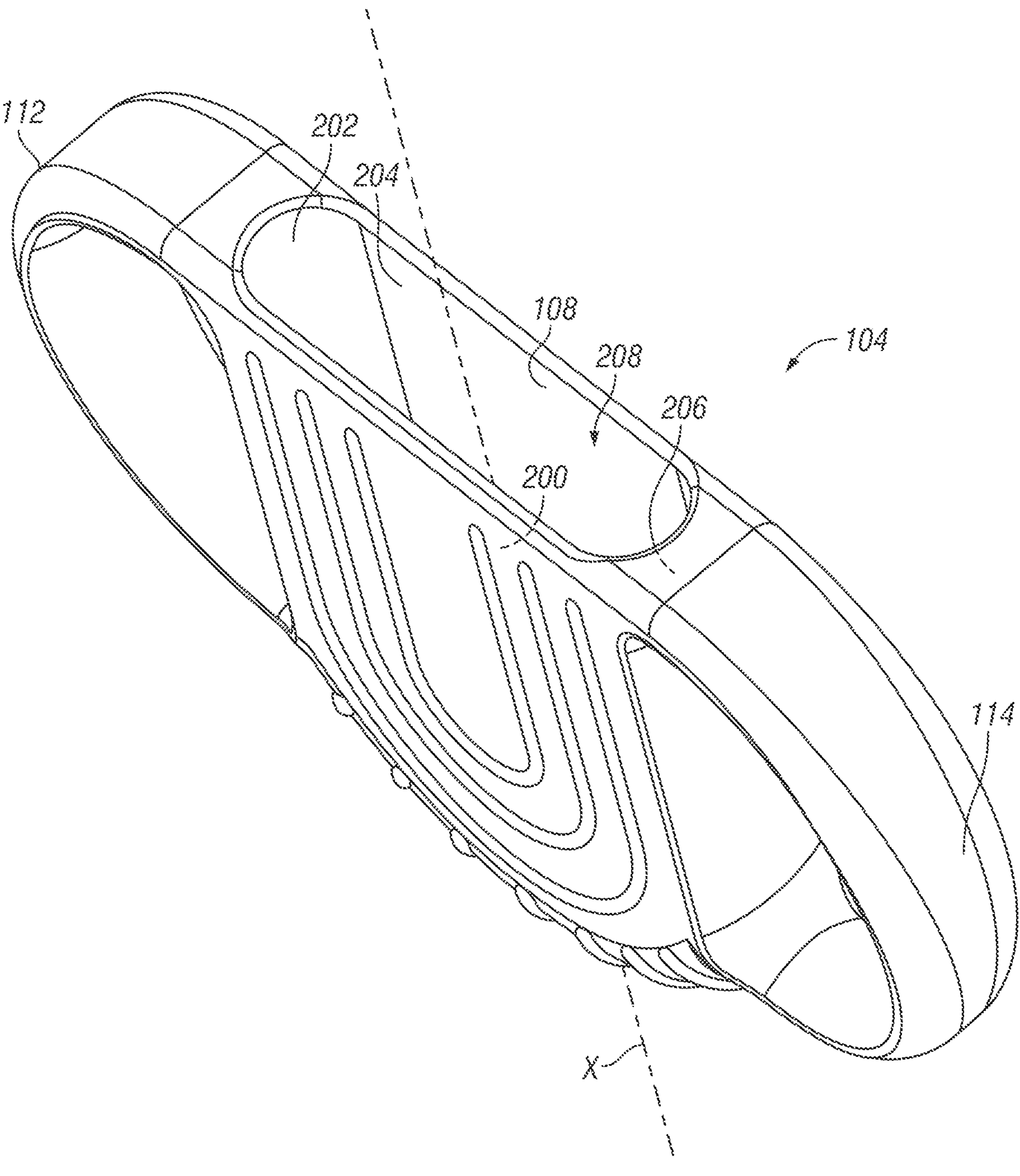
FIG. 2 is a perspective view of a handle prior to assembly to a biting element.
Figure 3:
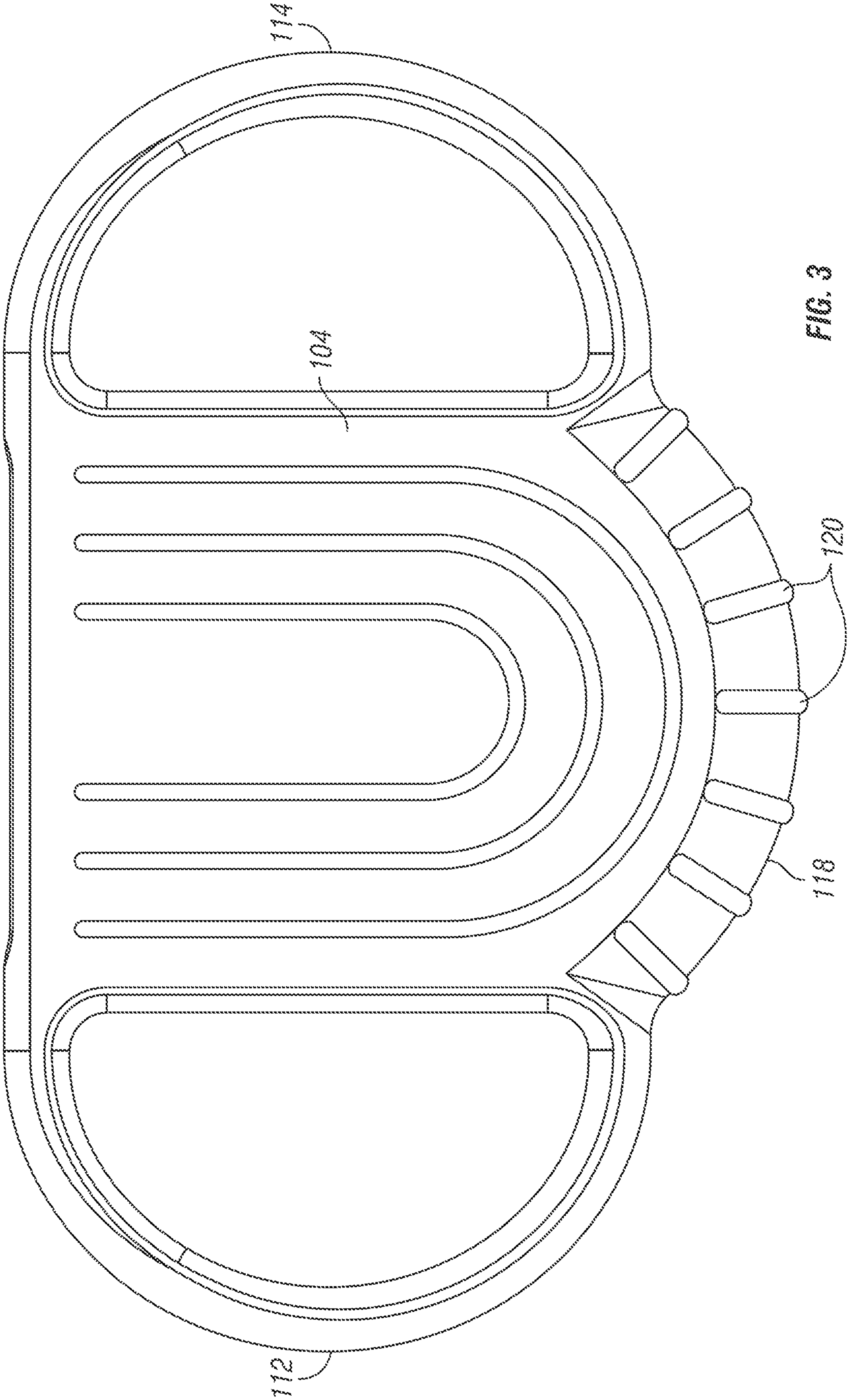
FIG. 3 is a front view of the handle shown in FIG. 2.

As seen in FIG. 2, in the illustrated embodiment the handle 104 is bilaterally symmetrical about an axis X. The receptacle 108 has a uniform cross-section throughout most of its depth. Receptacle 108 is defined by front wall 200 that is planar, a left sidewall 202 that is formed as a semicylinder, is straight and is parallel to axis X, a rear wall 204, and a right sidewall 206 that is formed as a semicylinder, is straight and is parallel to axis X. As so formed, receptacle 108 is adapted to have slid into it any of a plurality of biting elements including biting element 106. In the illustrated embodiment, the cross-section of the receptacle 108 takes the form of a flattened oval, but it could be rectangular or assume other shapes, so long as the cross section does not change from the receptacle opening 208 to a depth sufficient to house a biting element (described below).

Figure 4:
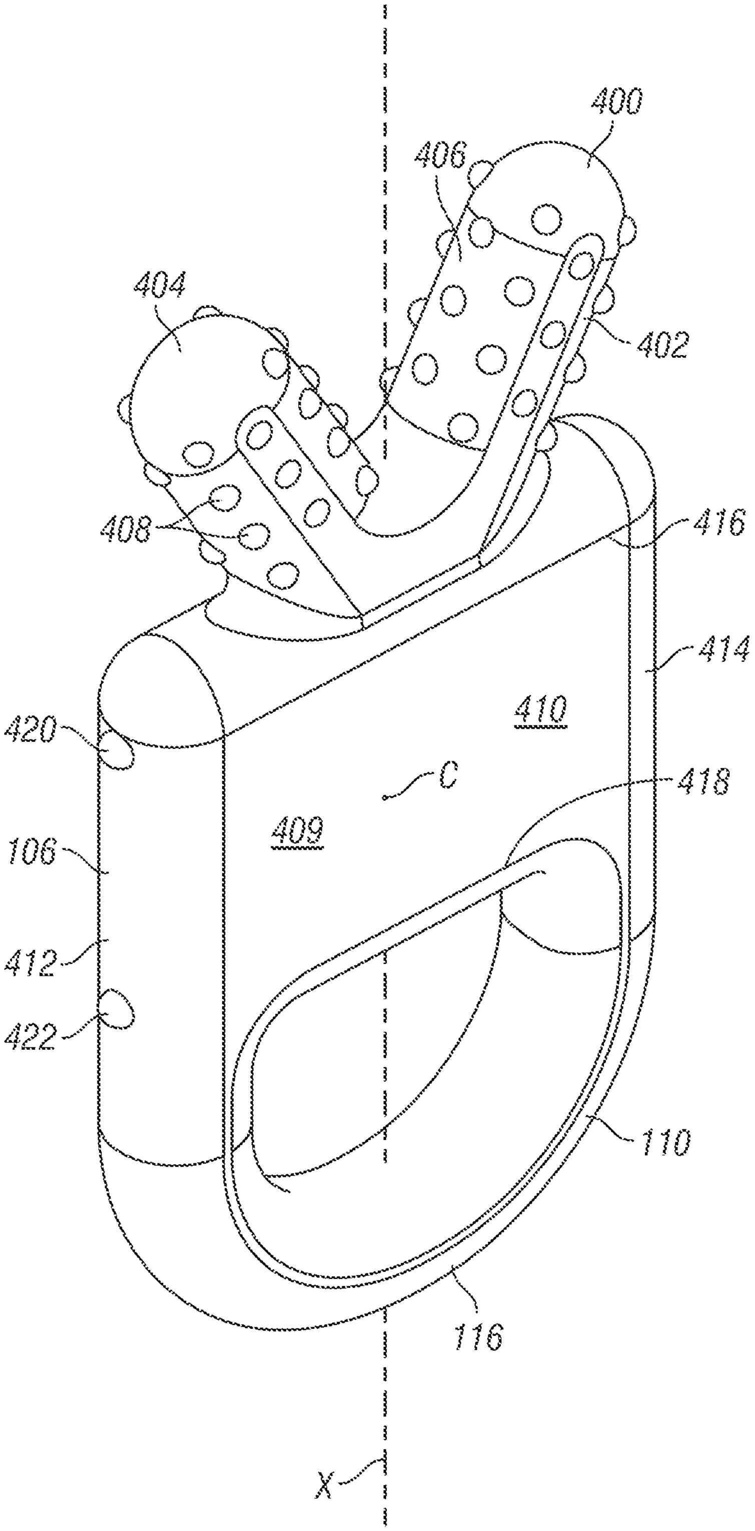
FIG. 4 is a perspective view of a first biting element.

The first biting element 106 is seen in more detail in FIG. 4. The biting element 106 has a second end portion 400 that extends in an opposed direction from first end portion 110, relative to a center C that in turn is located on axis X. In other embodiments, several such portions could radiate from center C in different directions. The second portion 400 has a second teething surface 402 that is different in shape and in texture from first teething surface 116. In the illustrated embodiment, the first teething surface 116 takes the form of a smooth, semicircular ring, while the second teething surface 402 is composed of fingers 404, 406 that stick out in different directions. The second teething surface 402 further is not smooth but instead has a population of spaced-apart nubs 408 on its surface. Teething surface 402 is therefore different both in shape and in texture from teething surface 116.

The first portion 116 and the second portion 400 extend in opposite directions from a biting element body 409. The biting element body 409 has a flat front wall 410, a flat rear wall that is a mirror image of the front wall 410, a straight and semicylindrical left sidewall 412, and a straight and semicylindrical right sidewall 414. Any cross section of the element body 409 from a top end 416 to a bottom end 418 thereof will be substantially uniform and will substantially match, in shape, the cross section of handle receptacle 108. The cross section of receptacle 108 and the cross section of body 409 may take shapes other than those shown, but they should be similar in shape to each other.

Two nubs or bumps 420, 422 project laterally outwardly from left sidewall 412, The bumps 420, 422 are intentional departures from the shape of the handle receptacle 108, and are adapted to engage left receptacle sidewall 202 with an interference fit. Bumps 420, 422 are spaced apart from each other and are so positioned that when the first biting element is fully inserted into receptacle 108, both bumps 420, 422 will be engaging left receptacle sidewall 202. Similar bumps (not visible in this figure; see 606 and 608 in FIG. 6) are disposed in corresponding positions on the right body sidewall 414 and project laterally rightward to frictionally engage with the receptacle sidewall 206. A distance in parallel to axis X from top end 416 to bottom end 418 should be no more than a depth of the straight sidewalls 202, 206 of receptacle 108.

Figure 5:
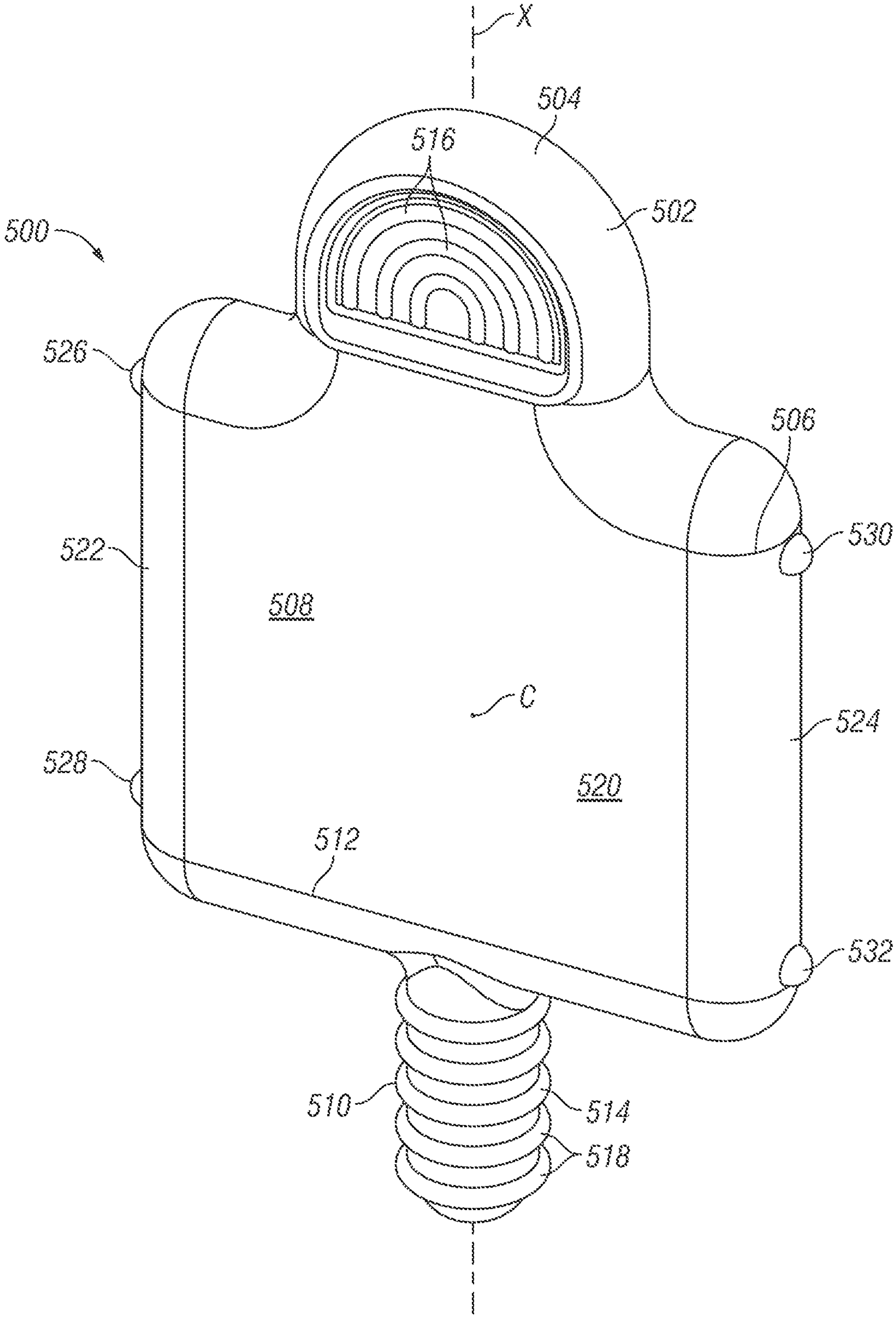
FIG. 5 is a perspective view of a second biting element.

A second biting element is indicated generally at 500 in FIG. 5. Biting element 500 has a first portion 502 with a first teething surface 504. The first portion 502 extends in one direction, along axis X, from a top end 506 of a rectangular body 508. In the illustrated embodiment, biting element 500 is substantially bilaterally symmetrical around axis X. A second portion 510 of the biting element 500 extends, in a second direction along axis X that is opposite from the first direction, from a bottom end 512 of the body 508. Second portion 510 has a second teething surface 514. In the illustrated embodiment, teething surfaces 504 and 514 differ from each other in both shape and texture. Teething surface 502 takes the form of a semicircular disk and has a series of concentric curved ribs 516 on its front face (shown) and on its rear face (a mirror image of the front face). Teething surface 514 takes the form of a single axially extending finger and has a series of projecting, circumaxial rings 518.

Body 508 has a flat front face 520 and a rear face that is a mirror image of the front face 520. A left, straight, semicylindrical sidewall 522 is parallel to axis X. A right, straight, semicylindrical sidewall 524 is disposed in opposition to sidewall 522 and is also parallel to axis X. A cross section of body 508 taken anywhere between top end 506 and bottom end 512 thereof will be substantially uniform, and will match the shape of the cross section of handle receptacle 108.

A top nub or bump 526 projects laterally leftward from sidewall 522, as does a bottom nub or bump 528. Nubs 526 and 528 are spaced apart from each other by a distance that is less than the depth of the straight sidewall 202 of receptacle 108. This ensures that both nubs 526 and 528 will frictionally engage sidewall 202 when the biting element 500 is fully inserted into handle receptacle 108. Similarly, a top nub or bump 530 projects laterally rightward from right body sidewall 524, as does a bottom nub or bump 532. Nubs 530, 532 are adapted to frictionally engage the right sidewall 206 of receptacle 108. The spacing between nubs 530 and 532 are such that both will be engaging sidewall 206 when the biting element 500 is fully inserted into the handle receptacle 108, and can match the spacing and position of nubs 526, 528, as shown.

Figure 6:
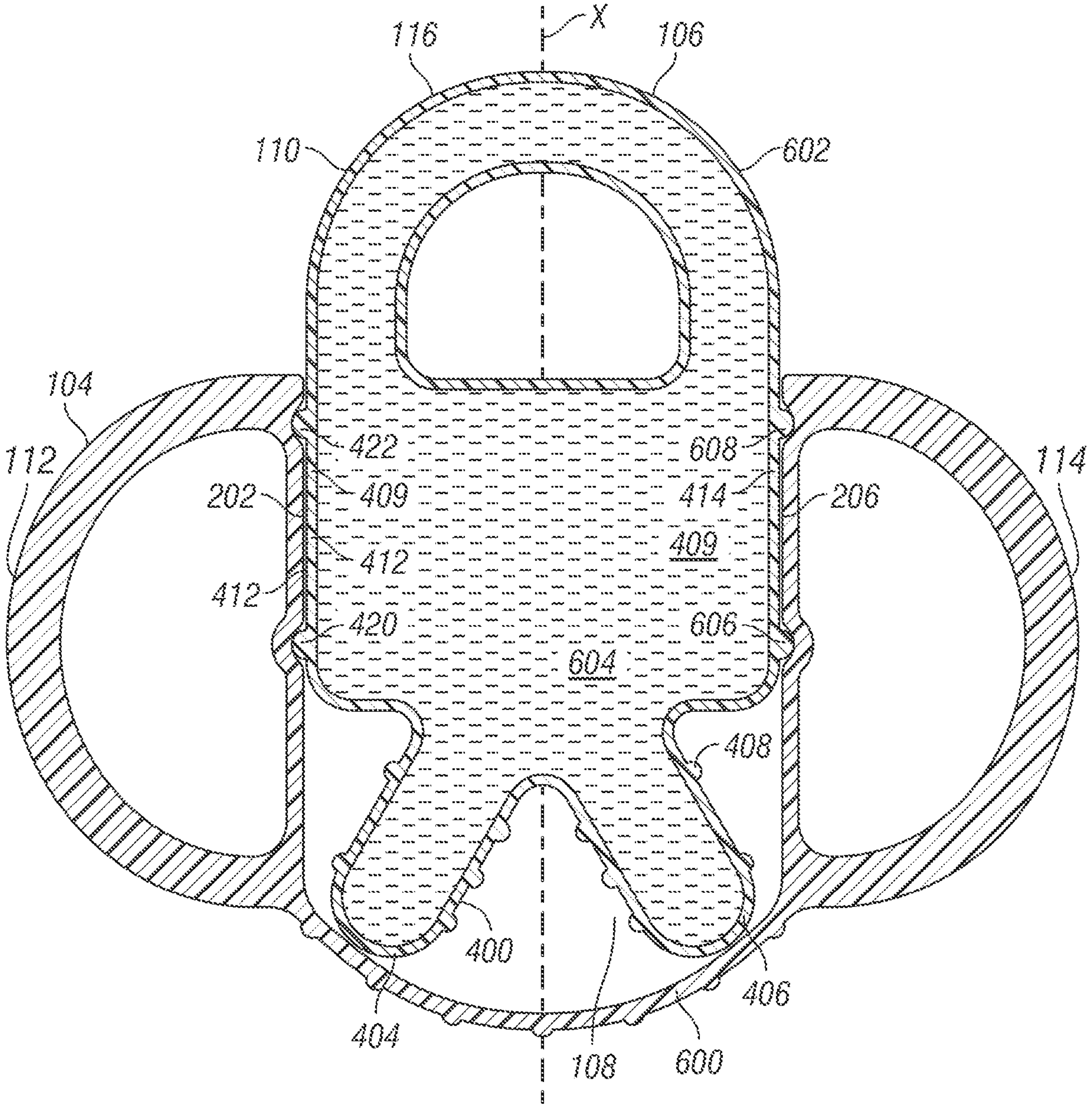
FIG. 6 is front sectional view, taken substantially along a plane including the assembly axis, showing the first biting element assembled to the handle.

FIG. 6 is a front sectional view showing biting element 106 as assembled to the handle 104. As assembled, the body 409 and second portion 400 of the biting element 106 have been fully slid or inserted into receptacle 108. The receptacle 108 has an outwardly convexly curved bottom 600 that is deep enough to accommodate fingers 404 and 406. The biting element 106 can also be assembled to handle 104 such that body 409 and first portion 110 are within the handle receptacle 104, leaving second portion 400 exposed. In that condition, curved bottom 600 is deep enough to accommodate the semicircular ring shape of first teething surface 116.

Alternatively, second biting element 500 may be assembled to handle 104. Either first teething surface 504 or second teething surface 514 is selected for use, and the nonselected teething surface and portion, and body 508, are inserted into the receptacle 108. The curved bottom 600 is large enough to accommodate the semicircular disk 514 or the single finger 514, as needed.

Notice that in any of the four assembly possibilities in the illustrated embodiment, a major portion of the selected biting element is covered or shrouded by the handle 104. This major portion preferably includes the biting element body 409, 508, and an unselected one of the two end portions 110, 400, 502, 510 of the biting element. It is this major portion of the biting element that is insulated from the hands of the child and which therefore will not cause discomfort to the child even if cooled.

In the illustrated embodiment, each of the biting elements 106, 500 is hollow. A sidewall of either biting element (sidewall 602 of biting element 106 is shown in FIG. 6) is integrally molded, as by blow molding, from a nontoxic polymer compound. Preferably this polymer compound is an elastomer, and more preferably it is silicone rubber. In the illustrated embodiment an interior 604 of the biting element is filled with a substance that is liquid at an ambient temperature $T_A$. Temperature $T_A$ may, for example, be 20 C. The substance should be nontoxic and may, for example, be a gel composed of water, propylene glycol, phenoxyethanal and acrylamide-acrylic copolymer. In one embodiment, this substance changes to a solid phase at a cooled temperature $T_C$ that is less than $T_A$. Cooled temperature $T_C$ may, for example, be −5 C, or another cooled temperature typically found in domestic freezers. In another embodiment, the cooled temperature is one typically found in domestic refrigerators, such as 3 C.

In those embodiments where the contained liquid becomes frozen at cooled temperature $T_C$, its heat of fusion is available to keep the biting element cooler for a longer period of time. This is because much more heat from the child is required to melt the substance than is needed to simply elevate its temperature within a particular phase.

In FIG. 6, it can be seen that bump or nub 420 extends laterally to the left from the generally straight semicylindrical left sidewall 412 of the biting element 106, and that bump or nub 422 also extends laterally to the left from the otherwise straight sidewall 412. In a similar fashion, a bump or nub 606 extends laterally to the right from otherwise straight semicylindrical right sidewall 414. A further bump or nub 608 also extends laterally to the right from the sidewall 206. The positioning and spacing of nubs 420, 422; 606, 608 is such that when the biting element is fully inserted into the receptacle 108, either portion 400 first (as shown in FIG. 6) or portion 110 first, the nubs 420, 422, 606, 608 will be in interference with the receptacle sidewalls 202, 206. In those embodiments in which the sidewalls 202, 206 are molded from an elastomer, each bump 420, 422, 606, 608 will cause a respective local dislocation of the receptacle sidewall 202, 206, as shown. Where biting element 500 is selected, bumps 526, 528, 530 and 532 will cause similar dislocations. These interferences prevent the inadvertent separation of the selected biting element from the handle. The caregiver will be able to pull the selected biting element out of the handle receptacle, but the child will have difficulty in doing so.

In an alternative embodiment (not shown), sockets could be formed in the receptacle sidewalls 202, 206 at appropriate positions to receive respective ones of the biting element nubs 420, 422, 606, 608. Those sockets would perform a detenting function with the respect to the inserted biting element.

Biting elements with teething surfaces different in shape or texture from surfaces 116, 402, 504 and 514 may be provided, in substitution of or in addition to the teething surfaces shown. Teething systems according to the invention may have one, two or more biting elements. In each case the end portions on which such teething surfaces are formed should fit within the handle receptacle 108. In another embodiment, one or more biting elements could be provided in which only one of the two end portions is provided with a teething surface, the other end portion merely acting as an insert plug for the handle receptacle 108.

Figure 7:
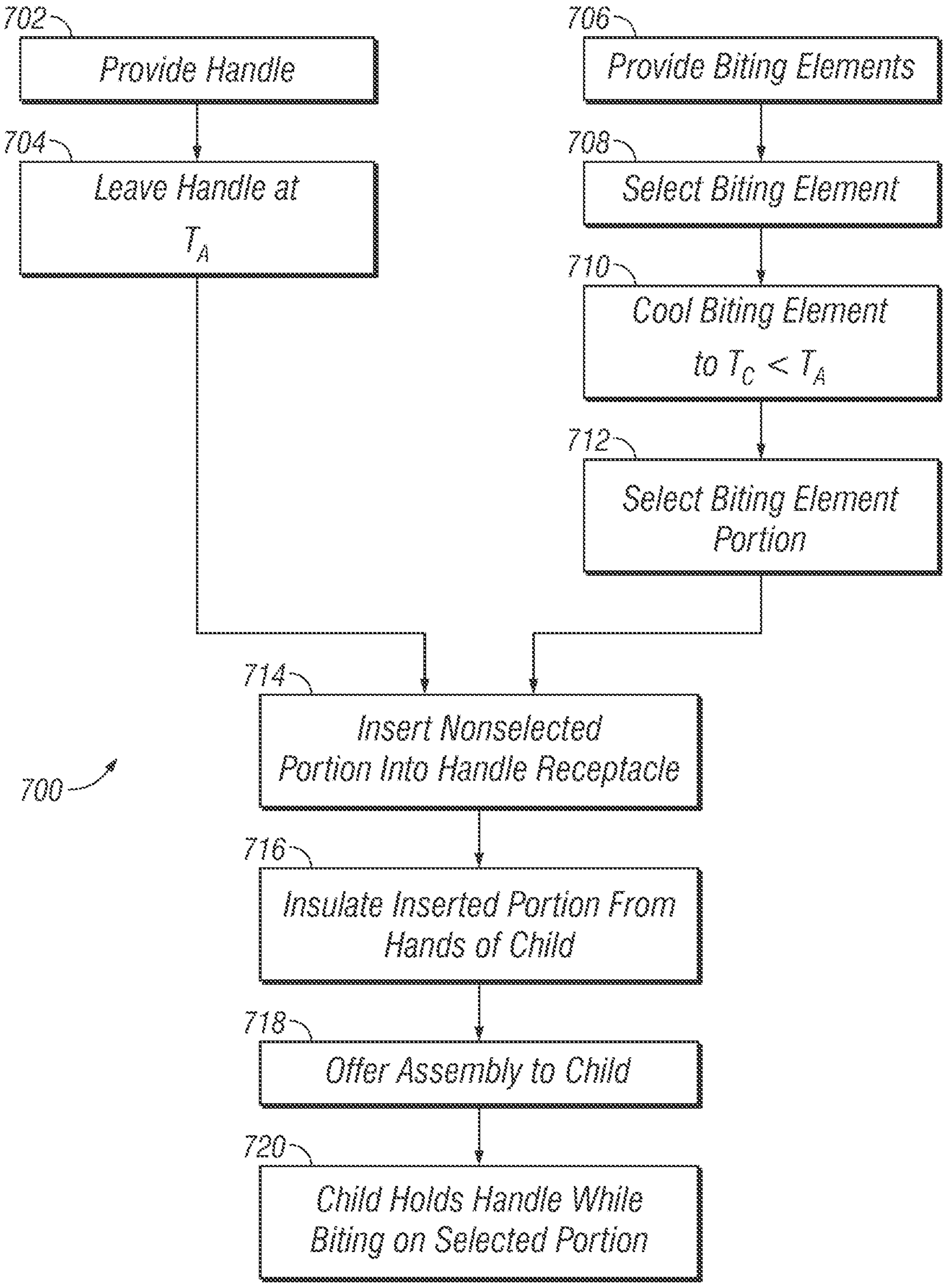
FIG. 7 is a flow chart depicting steps in a method of use according to the invention.

FIG. 7 illustrates steps of a method 700 for use of the invention. At step 702, a handle with a receptacle is provided. This handle is (704) left at ambient temperature $T_A$. At step 706, one or more biting elements are provided. The caregiver selects one of these biting elements at step 708. At step 710, the caregiver cools the selected biting element to a cooled temperature $T_C$, as by placing the biting element in a refrigerator or freezer.

Once the biting element has been cooled, and for those biting elements which have more than one end portion and teething surface, at step 712 the caregiver selects which portion of the biting element will be presented to the child. Then, at step 714, the nonselected portion of the biting element is inserted into the handle receptacle. Preferably and at this time the biting element body is also inserted into the handle receptacle. Responsive to this step, and at step 716, the inserted portion of the biting element is insulated from the hands of the child.

As so assembled, and at step 718, the assembled handle and biting element are offered to the child. At step 720, the child holds the handle with his or her hands, while biting on the portion of the biting element that the caregiver has selected for use. The child thus may soothe his or her sore teeth and gums with a cooled surface, while at the same time may hold the handle of the teething system in comfort.

In summary, a teething system has been shown and described that includes a handle with a handle receptacle and one or more biting elements. The handle is left at room temperature while a selected biting element is cooled. After cooling, a major portion of the biting element is inserted into the handle receptacle, insulating this portion from the hands of the child. A selected portion of the biting element remains exposed and is operable to give the child cooling relief while the child comfortably holds the handle.

While illustrated embodiments of the present invention have been described and illustrated in the appended drawings, the present invention is not limited thereto but only by the scope and spirit of the appended claims.

We claim:

1. A teething system comprising:

a handle disposed on an axis and adapted to be grasped by a hand of a child, the handle having a receptacle with an open end and adapted to be left at an ambient temperature, the receptacle having a substantially uniform cross section from the open end through a predetermined depth, the cross section of the receptacle having a shape;

a first biting element disposed on the axis and having a body, a first portion extending from the body and a second portion extending from the body, the body having a substantially uniform cross section across a length of the body with a shape that substantially matches the shape of the cross section of the receptacle, the first biting element adapted to be cooled to a cooled temperature below ambient temperature, the second portion and the body together being a major portion of the first biting element and adapted to be slid along the axis into the receptacle, the first portion of the first biting element presenting a first teething surface on which the child may bite;

the handle adapted to cover the second portion of the first biting element when the second portion is slid into the receptacle, such that the handle insulates the child's hand from the cooled second portion of the first biting element.

2. The system of claim 1, wherein, the first teething surface is selected from the group consisting of a single finger of reduced cross section extending from the body, at least two fingers of reduced cross section extending from the body in different directions, a semicircular disk extending from the body, and a semicircular ring extending from the body.

3. The system of claim 1, wherein the receptacle has a first length greater than a first width, the body of the first biting element having a second length greater than a second width, the second length being less than the first length, the second width being less than the first width.

4. The system of claim 1, wherein the receptacle of the handle and the body of the first biting element are formed to be substantially bilaterally symmetrical relative to the axis, a first substantially straight sidewall of the body formed in parallel to the axis, a first substantially straight sidewall of the receptacle formed in parallel to the axis, at least one first bump laterally extending from the first sidewall of the body, the first bump adapted to engage the first sidewall of the receptacle to create an interference fit.

5. The system of claim 4, wherein a second substantially straight sidewall of the body is formed in parallel to the axis and in opposition to the first sidewall of the body, a second substantially straight sidewall of the receptacle formed in parallel to the axis and in opposition to the first sidewall the receptacle, at least one second bump laterally extending from the second sidewall of the body, the second bump adapted to engage the second sidewall of the receptacle to create an interference fit.

6. The system of claim 1, wherein the second portion of the first biting element has a second teething surface of a different shape or texture than the first teething surface, the first portion of the first biting element adapted to be slid along the axis into the receptacle of the handle, a nonselected one of the first and second portions of the biting element being slid along the axis into the receptacle of the handle, a selected one of the first and second portions of the biting element being exposed such that a selected one of the first and second teething surfaces arc is available for the child to bite.

7. The teething system of claim 6, wherein the handle has formed thereon a third teething surface.

8. The teething system of claim 1, wherein the first biting element is hollow.

9. The teething system of claim 8, wherein the first biting element is filled with a substance that is liquid at ambient temperature.

10. The teething system of claim 9, wherein the substance is adapted to be frozen when cooled to the cooled temperature, a heat of fusion of the substance providing enhanced cooling to the first biting element.

11. A teething system comprising:

a handle disposed on an axis and having a receptacle, the receptacle having an open end, the receptacle having a substantially uniform cross-section from the open end through a predetermined depth, the cross section of the receptacle having a shape, the handle adapted to remain at an ambient temperature; and a first biting element disposed on the axis and having a body, first portion extending from the body and a second portion extending from the body, the body having a substantially uniform cross section across a length of the body with a shape that substantially matches the shape of the cross section of the receptacle, the first portion having a first teething surface on which a child may bite, the second portion having a second teething surface on which a child may bite, the second teething surface being different in shape or texture from the first teething surface, the first biting element adapted to be cooled to a cooled temperature below the ambient temperature;

the first portion and the second portion each adapted to be inserted along the axis into the receptacle, a nonselected one of the first and second portions inserted into the receptacle during use, such that the nonselected one of the first and second portions is shrouded from contact by the hands of the child, and such that a selected one of the first and second teething surfaces is exposed for the child to bite.

12. The teething system of claim 11, wherein the first biting element is formed around a center, the first portion of the first biting element extending from the center in a first direction, the second portion of the first biting element extending from the center in a second direction 180 degrees from the first direction.

13. A teething system comprising:

a handle having an axis and a receptacle with an open end, the receptacle having a substantially uniform cross section from the open end through a predetermined depth, the cross section of the receptacle having a shape, the handle adapted to remain at ambient temperature;

a plurality of biting elements including first and second biting elements, the first and second biting elements adapted to be cooled to a cooled temperature below the ambient temperature, the first biting element having a first body, a first portion extending from the first body with a first teething surface on the first portion and a second portion extending from the first body, the first body having a substantially uniform cross section across a length of the first body with a shape that substantially matches the shape of the cross section of the receptacle, the second portion adapted to be inserted along the axis into the receptacle, the second biting element having a second body, the second body having a substantially uniform cross section across a length of the second body with a shape that substantially matches the shape of the cross section of the receptacle, a third portion extending from the second body with a second teething surface on the third portion thereon and a fourth portion extending from the second body and adapted to be inserted into the receptacle along the axis, the first teething surface having a shape or texture different from that of the second teething surface;

a selected one of the second and fourth portions being inserted along the axis into the receptacle of the handle in order to assemble a selected one of the first and second biting elements to the handle, a selected one of the first and second teething surfaces thereby being exposed to a child to bite while a selected one of the second and fourth portions is shrouded from the hands of the child by the handle, so that the child does not experience discomfort in grasping the handle, while at the same time being able to bite a cooled teething surface.

14. The teething system of claim 13, wherein the receptacle has a substantially straight sidewall formed in parallel to the axis;

the first body having a substantially straight first body sidewall formed in parallel to the axis, at least one first bump laterally extending from the first body sidewall and adapted to engage the sidewall of the receptacle to create an interference fit; and the second body having a substantially straight second body sidewall formed in parallel to the axis, at least one second bump laterally extending from the second body sidewall and adapted to engage the sidewall of the receptacle to create an interference fit.

15. A method for providing relief to a child from teething pain, the method comprising the steps of:

providing a handle disposed on an axis that has a receptacle with an open end, the receptacle having a substantially uniform cross section from the open end through a predetermined depth, the cross section of the receptacle having a shape;

leaving the handle at ambient temperature;

providing a first biting element disposed on the axis, the first biting element having a first body, a first portion extending from the first body and a second portion extending from the first body, the first body having a substantially uniform cross section across a length of the first body with a shape that substantially matches the shape of the cross section of the receptacle, the first portion having a teething surface on which the child may bite, the second portion adapted to be slid into the receptacle of the handle, the second portion and the first body together being a major portion of the first biting element;

cooling the first biting element to a cooled temperature below ambient temperature;

sliding the second portion of the first biting element along the axis into the receptacle of the handle, so as to assemble the first biting element to the handle;

as a result of said step of sliding, insulating the second portion of the cooled first biting element from a hand of the child; and offering the assembled handle and first biting element to the child, the child capable of grasping the handle while biting on the teething surface of the first biting element, thereby avoiding discomfort which would otherwise be caused by the cooled first biting element coming into contact with the child's hand, while at the same time providing cooling relief to the mouth of the child.

16. The method of claim 15, further comprising the steps of:

providing a second biting element, the second biting element having a second body, a third portion extending from the second body and a fourth portion extending from the second body, the second body having a substantially uniform cross section across a length of the second body with a shape that substantially matches the shape of the cross section of the receptacle, the third portion of the second biting element having a second teething surface on which the child may bite, the fourth portion of the second biting element adapted to be slid along the axis into the receptacle of the handle;

selecting one of the first and second biting elements for use;

cooling the selected biting element to a cooled temperature below ambient temperature;

sliding a selected one of the second and fourth portions along the axis into the receptacle of the handle, to thereby assemble the selected biting element to the handle;

as a result of said step of sliding, insulating a selected one of the second and fourth portions from the hand of the child, thereby avoiding discomfort to the child; and offering the assembled handle and selected biting element to the child.

17. The method of claim 15, further comprising the steps of:

forming the receptacle to have a substantially straight sidewall in parallel to the axis;

forming the first body of the first biting element to have a substantially straight first body sidewall in parallel to the axis, at least one first bump laterally extending from the first body sidewall; and during said step of sliding the second portion of the first biting element into the receptacle of the handle, engaging the sidewall of the receptacle with the at least one first bump so as to create an interference fit.

18. A method for providing relief to a child from teething pain, comprising the steps of:

providing a handle disposed on an axis that has a receptacle with an open end, the receptacle having a substantially uniform cross section from the open end through a predetermined depth, the cross section of the receptacle having a shape;

leaving the handle at ambient temperature;

providing a first biting element disposed on the axis, the first biting element having a first body, a first portion extending from the first body and a second portion extending from the first body, the first portion having a first teething surface on which the child may bite and the second portion having a second teething surface on which the child may bite, the first body having a substantially uniform cross section across a length of the first body with a shape that substantially matches the shape of the cross section of the receptacle;

cooling the first biting element to a cooled temperature below the ambient temperature;

selecting one of the first and second portions of the first biting element for use;

after said step of cooling, sliding a nonselected one of the first and second portions of the first biting element along the axis into the receptacle of the handle, to thereby assemble the first biting element to the handle;

as a result of said step of sliding the nonselected one of the first and second portions of the first biting element into the receptacle of the handle, insulating the nonselected one of the first and second portions from the hand of the child; and offering the assembled first biting element and handle to the child, such that the nonselected one of the first and second portions of the first biting element is insulated from the child, while at the same time the selected one of the first and second portions of the first biting element is exposed for use.

* * * * *